(12) United States Patent
Swoboda et al.

(10) Patent No.: US 9,138,568 B2
(45) Date of Patent: Sep. 22, 2015

(54) CSF SHUNT FLOW ENHANCER, METHOD FOR GENERATING CSF FLOW IN SHUNTS AND ASSESSMENT OF PARTIAL AND COMPLETE OCCLUSION OF CSF SHUNT SYSTEMS

(75) Inventors: Marek Swoboda, Philadelphia, PA (US); Matias Gabriel Hochman, Philadelphia, PA (US); Mark Evan Mattiucci, Newton Square, PA (US); Frederick J. Fritz, Skillman, NJ (US); Joseph R. Madsen, Newton Center, MA (US)

(73) Assignees: ShuntCheck, Inc., Princeton, NJ (US); The Children's Medical Center Corporation, Boston, MA (US)

( * ) Notice: Subject to any disclaimer, the term of this patent is extended or adjusted under 35 U.S.C. 154(b) by 219 days.

(21) Appl. No.: 13/698,477

(22) PCT Filed: May 19, 2011

(86) PCT No.: PCT/US2011/037218
§ 371 (c)(1),
(2), (4) Date: Dec. 27, 2012

(87) PCT Pub. No.: WO2011/146757
PCT Pub. Date: Nov. 24, 2011

(65) Prior Publication Data
US 2013/0102951 A1   Apr. 25, 2013

Related U.S. Application Data

(60) Provisional application No. 61/396,044, filed on May 21, 2010, provisional application No. 61/458,969, filed on Dec. 6, 2010.

(51) Int. Cl.
*A61M 27/00* (2006.01)
(52) U.S. Cl.
CPC ........... *A61M 27/006* (2013.01); *A61M 27/002* (2013.01)

(58) Field of Classification Search
CPC . A61M 27/00; A61M 27/002; A61M 27/006; A61M 5/01; A61M 5/015; A61M 5/031
USPC ........................................ 604/8–10, 131–155
See application file for complete search history.

(56) References Cited

U.S. PATENT DOCUMENTS

| 4,548,516 A | 10/1985 | Helenowski |
| 5,255,979 A | 10/1993 | Ferrari |

(Continued)

FOREIGN PATENT DOCUMENTS

| JP | 07-275210 | 10/1995 |
| JP | 10-276993 | 10/1998 |

(Continued)

OTHER PUBLICATIONS

International Search Report for PCT/US2011/037218, Jan. 10, 2012.
(Continued)

*Primary Examiner* — Philip R Wiest
*Assistant Examiner* — Benjamin Klein
(74) *Attorney, Agent, or Firm* — Caesar Rivise, PC

(57) ABSTRACT

An apparatus capable of generating flow in cerebrospinal fluid (CSF) shunt systems by vibrating the shunt, tubing or shunt valve dome, or applying cyclical pressure to the various parts of the shunt system. A method of generating flow and method of using the apparatus in shunt patency assessment, for example, hydraulic resistance assessment, is also disclosed. The apparatus allows, in conjunction with a thermal dilution method or radionuclide method, a quick CSF shunt patency assessment based upon CSF shunt resistance and not upon CSF flow or intracranial pressure (ICP) separately. This provides a more objective measure of shunt obstruction compared to other methods. Furthermore, the apparatus can be used to enhance flow in shunts, identify partial occlusion before symptoms occur, differentiate between patent, partially-occluded and occluded shunts. The apparatus can be used to generate flow in shunts if there is a need to lower ICP or move drugs administered via an injection chamber or a shunt dome.

12 Claims, 12 Drawing Sheets

(56) References Cited

U.S. PATENT DOCUMENTS

| | | | |
|---|---|---|---|
| 7,520,862 | B2 | 4/2009 | Neff |
| 7,625,117 | B2 | 12/2009 | Haslett et al. |
| 8,075,470 | B2 | 12/2011 | Alekseyenko et al. |
| 8,302,471 | B2 | 11/2012 | Van Der Wiel |
| 8,551,101 | B2 | 10/2013 | Kuczynski |
| 8,894,584 | B2 | 11/2014 | Swoboda et al. |
| 2002/0035340 | A1 | 3/2002 | Fraden et al. |
| 2002/0121137 | A1 | 9/2002 | Fujiwara et al. |
| 2003/0004495 | A1 | 1/2003 | Saul |
| 2004/0068201 | A1 | 4/2004 | Saul |
| 2004/0147871 | A1* | 7/2004 | Burnett ............... 604/9 |
| 2005/0094707 | A1 | 5/2005 | Lee et al. |
| 2005/0149170 | A1 | 7/2005 | Tassel et al. |
| 2005/0171452 | A1 | 8/2005 | Neff |
| 2005/0204811 | A1 | 9/2005 | Neff |
| 2006/0000271 | A1 | 1/2006 | Bork |
| 2006/0235349 | A1 | 10/2006 | Osborn et al. |
| 2007/0073132 | A1 | 3/2007 | Vosch |
| 2007/0206655 | A1 | 9/2007 | Haslett et al. |
| 2007/0282218 | A1 | 12/2007 | Yarden |
| 2008/0039739 | A1 | 2/2008 | Buja |
| 2008/0150682 | A1 | 6/2008 | Shii |
| 2008/0207984 | A1 | 8/2008 | Alekseyenko et al. |
| 2008/0214951 | A1* | 9/2008 | Fritz et al. ............ 600/549 |
| 2010/0228179 | A1 | 9/2010 | Thomas et al. |
| 2011/0054382 | A1 | 3/2011 | Fritz et al. |

FOREIGN PATENT DOCUMENTS

| | | |
|---|---|---|
| JP | 2004-513681 | 5/2004 |
| JP | 2006-017722 | 1/2006 |
| JP | 2008-032544 | 2/2008 |
| JP | 2009-189815 | 8/2009 |
| WO | WO 02/07596 | 7/2002 |
| WO | WO 2008-127867 A2 | 10/2008 |
| WO | WO 2009-146075 A1 | 12/2009 |
| WO | WO 2011-150323 | 12/2011 |

OTHER PUBLICATIONS

International Search Report for corresponding PCT Application No. PCT/US2009/039146, dated Oct. 1, 2009.
International Search Report for related PCT Application No. PCT/US2011/038317 dated Feb. 24, 2012.
International Search Report for related PCT Application No. PCT/US2013/052018 dated Nov. 6, 2013.
International Search Report for related PCT Application No. PCT/US2013/071928 dated Mar. 6, 2014.
Bech-Azeddine, et al., "Idiopathic Normal-Pressure Hydrocephalus: Clinical Comorbidity Corrected With Cerebrospinal With Cerebral Biopsy Findings and Outcome of Cerebrospinal Fluid Shunting", Journal of Neurology, Neurosurgery & Psychiatry, vol. 78, pp. 157-161, 2007.
Cohen, M., "Measurement of the Thermal Properties of Human Skin. A Review", The Journal of Investigative Dermatology, vol. 69, No. 3, pp. 333-338, 1977.
Drake J., et al., "Cerebrospinal Fluid Flow Dynamics in Children with External Ventricular Drains", Neurosurgery, vol. 28, No. 2, pp. 242-250, 1991.
Drake, J., et al., "Randomized Trial of Cerebrospinal Fluid Shunt Calve Design in Pediatric Hydrocephalus", Neurosurgery, vol. 43, Issue 2, pp. 1-39, Aug. 1998.
Eggleston, T., et al., "Comparison of Two Porcine (*Sus scrofa domestica*) Skin Models for in Vivo Near-Infrared Laser Exposure", Comparative Medicine, vol. 50, No. 4, pp. 391-397, Aug. 2000.
Hidaka M., et al., "Dynamic Measurement of the Flow Rate in Cerebrospinal Fluid Shunts in Hydrocephalic Patients", European Journal of Nuclear Medicine, vol. 28, No. 7, pp. 888-893, Jul. 2001.
Iskandar, B., et al., "Death in Shunted Hydrocephalic Children in the 1990s", Pediatric Neurosurgery, vol. 28, pp. 173-176, Apr. 1998.
Iskandar, B., et al., "Pitfalls in the Diagnosis of Ventricular Shunt Dysfunction: Radiology Reports and Ventricular Size", Pediatrics, vol. 101, No. 6, pp. 1031-1036, Jun. 1998.
Kestle, J., et al., "Lack of Benefit of Endoscopic Ventriculoperitoneal Shunt Insertion: A Multicenter Randomized Trial", Journal of Neurosurgery, vol. 98, pp. 284-290, Feb. 2003.
Laurence, K., et al., "The Natural History of Hydrocephalus", Archives of Disease in Childhood, pp. 345-362, Apr. 1962.
McGirt, M., et al., "Cerebropsinal Shunt Survival and Etiology of Failures: A Seven-Year Institutional Experience", Pediatric Neurosurgery, vol. 36, No. 5, pp. 248-255, May 2002.
Patwardhan, N., et al., "Implanted Ventricular Shunts in the United States: The Billion Dollar a Year Cost of Hydrocephalus Treatment", Neurosurgery, vol. 56, No. 1, pp. 139-145, Jan. 2005.
Piatt, J., "Physical Examination of Patients with Cerebrospinal Fluid Shunts: Is There Useful Information in Pumping the Shunt?", Pediatrics, vol. 89, pp. 470-473, Mar. 1992.
Pitteti, R., "Emergency Department Evaluation of Ventricular Shunt Malfunction: Is the Shunt Series Really Necessary?", Pediatric Emergency Care, vol. 23, No. 3, pp. 137-141, Mar. 2007.
Sood S., et al., "Evaluation of Shunt Malfunction Using Shunt Site Reservoir", Pediatric Neurosurgery, vol. 32, pp. 180-186, 2000.
Ventureyra, E., et al., "A New Ventricular Catheter for the Prevention and Treatment of Proximal Obstruction in Cerebrospinal Fluid Shunts", Neurosurgery, Issue 34(5), pp. 924-926, May 1994.
Zorc, J., et al., "Radiographic Evaluation for Suspected Cerebrospinal Fluid Shunt Obstruction", Pediatric Emergency Care, vol. 18, No. 5, pp. 337-340, 2002.
Stein, et al., "A Noninvasive Approach to Quantitive Measurement of Flow Through CSF Shunts," J. Neurosurg., vol. 54, Apr. 1981.

* cited by examiner

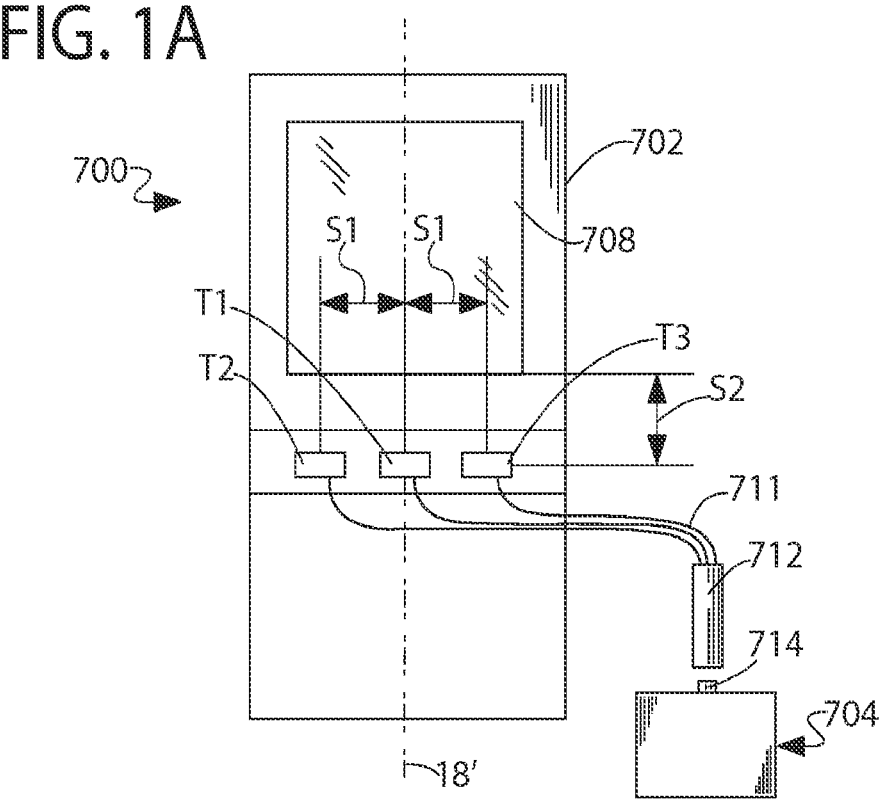
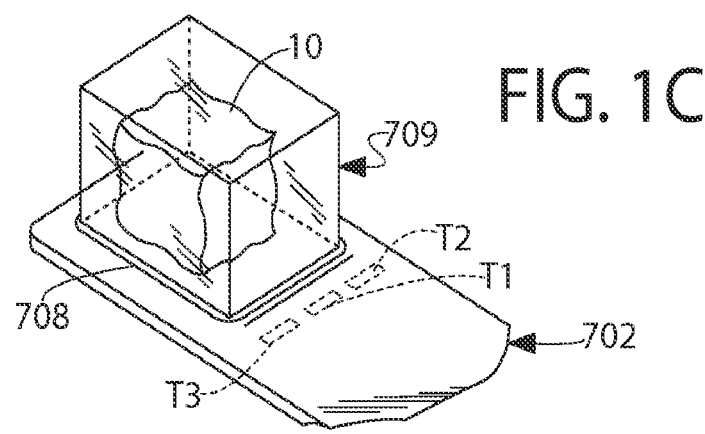

CSF SHUNT FLOW ENHANCER, METHOD FOR GENERATING CSF FLOW IN SHUNTS AND ASSESSMENT OF PARTIAL AND COMPLETE OCCLUSION OF CSF SHUNT SYSTEMS

CROSS-REFERENCE TO RELATED APPLICATIONS

This PCT application claims the benefit under 35 U.S.C. §119(e) of Provisional Application Ser. No. 61/396,044 filed on May 21, 2010 entitled CSF SHUNT FLOW ENHANCER, METHOD FOR GENERATING CSF FLOW IN SHUNTS AND ASSESSMENT OF PARTIAL AND COMPLETE OCCLUSION OF CSF SHUNT SYSTEMS and under 35 U.S.C. §119(e) of Provisional Application Ser. No. 61/458,969 filed on Dec. 6, 2010 entitled SHUNT OCCLUSION DETECTION DEVICE and all of whose entire disclosures are incorporated by reference herein.

STATEMENT REGARDING FEDERALLY SPONSORED RESEARCH OR DEVELOPMENT

This invention was made with government support under R43NS067772, R43HD065429and R44NS067772 awarded by the National Institutes of Health. The government has certain rights in the invention.

BACKGROUND OF THE INVENTION

1. Field of Invention

This present invention generally relates to cerebrospinal fluid shunts and, more particular, to a device and method for testing for the presence, absence and/or rate of flow in the shunt tubing implanted under the skin.

2. Description of Related Art

The Surgical Management of Hydrocephalus

Hydrocephalus is a condition of abnormal cerebrospinal fluid (CSF) homeostasis, resulting in an accumulation of CSF in the brain ventricles. Approximately 69,000 people are diagnosed with hydrocephalus each year in the United States, most commonly as a congenital condition, making it one of the most common birth defects [1]. Untreated hydrocephalus leads to progressive neurological dysfunction and death.

The most commonly used treatment for hydrocephalus is diversion of CSF from the ventricles to the peritoneal cavity by means of a permanent prosthetic shunt. A CSF shunt is comprised of a valve connected to a tube. The proximal end of the tube is surgically inserted into the ventricle of the brain, and runs subcutaneously through the body into the abdominal cavity (FIG. 4). There are approximately 300,000 shunted hydrocephalus patients in the US. 41,000 [3] shunt procedures are performed each year, approximately 12,000 of which are new shunt placements [4].

Improved materials, diagnostic, and treatment technologies, have improved shunt therapy since the 1970s [14]. However, shunt failure is still almost inevitable during a patient's life. The one-year failure rate of ventriculoperitoneal shunts has been estimated to be approximately 40% [15, 16], and the mean period to failure of an implanted shunt is typically only 5-10 years [17]. Obstruction of the ventricular catheter, usually from tissue ingrowth or clots, is overwhelmingly the greatest cause of shunt failure [4, 15, 18-20]. Shunt failure can rapidly progress to life-threatening elevation in intracranial pressure, so revision surgery, and re-placement of the blocked ventricular catheter is indicated. More than half of all shunt procedures in the United States are revisions [1, 4].

However, since catheter replacement surgery carries risks of life-threatening complications such as infection or embolism, a need for shunt revision needs to be reasonably established. The problem is that the usual clinical manifestations of shunt failure, such as headaches, vomiting, or loss of vision, are non specific and are difficult to differentiate from common, less serious illnesses, particularly in pediatric patients. This leads to two extremes of management: patient families who present persistently at emergency rooms for every headache or flu symptom, and patient families who dangerously dismiss symptoms of a shunt blockage as a common ailment. A study at the Children's Hospital of Philadelphia (CHOP) [4] indicates that three false alarms are seen for every true shunt malfunction. There is a need for objective methods to evaluate suspected shunt obstruction.

New Methods for Diagnosing Shunt Obstruction are Needed

An unacceptably high number of hydrocephalic children still die as a result of shunt malfunction, primarily because of a failure to identify shunt blockage at an early stage [14]. The early diagnosis of shunt obstruction is complex and difficult. While a number of shunt flow detection methods are available, none are diagnostic when used alone or are without complication, and there is little standardization to guide physicians in their interpretation (Table 1). Physical examination of the patient, including pumping of the shunt reservoir, is unreliable [21]. Measuring CSF pressure by "shunt tap" is invasive, painful, and can be misleading [22, 23]. CT (computed tomography) and MR (magnetic resonance), either alone, or in combination with plain radiographs, remain the gold standards for diagnosis of shunt malfunction [4, 9]. However, these imaging techniques are static, and so must be performed multiple times to detect ventricular enlargement. This results in repeated radiological exposures of patients (often children), a safety concern for pediatric neurosurgeons [40]. Furthermore, the reliability of these techniques for detecting CSF accumulation has been questioned [9, 24]. For a while, radionuclide markers were widely used to derive truly dynamic information about CSF flow in the brain and in shunts [25-27]. However, their promise was never wholly realized, and they are not routinely utilized in most clinical settings. Because of the expense and technical complexity of advanced imaging techniques, they cannot be used to investigate every headache.

TABLE 1

Performance of commonly used diagnostic procedures for suspected CSF shunt obstruction

| Diagnostic Procedure | Sensitivity (Detecting No Flow) | Specificity (Detecting Flow) | Features |
|---|---|---|---|
| Static Imaging Procedures | | | |
| CT Scan [36] | 68% | 90% | Expensive, time-consuming, radiation dose. Shunt malfunction must have gone on long enough for the scan to detect visible changes, i.e. ventricle enlargement. Rising concern about radiation. |

TABLE 1-continued

Performance of commonly used diagnostic procedures for suspected CSF shunt obstruction

| Diagnostic Procedure | Sensitivity (Detecting No Flow) | Specificity (Detecting Flow) | Features |
|---|---|---|---|
| X-ray Series [36] | 27% | 99% | Expensive and time-consuming. As with CT, the shunt must have malfunctioned long enough for visible changes to be detected. |
| | | | Dynamic Flow Measurements |
| Shunt Tap [37] | 79% | 56% | Method is painful, risks infection and can be inconclusive if blockage is upstream of the tap area. |
| Radio Isotope [38] | 80% | 53% | Requires an invasive shunt tap and 24 hours lead time for isotope. This method is considerably more involved than either the CT or MRI. |

The current, non-invasive imaging procedures have relatively low sensitivity and better specificity—making them reasonable rule-in tests but poor rule-out tests. The invasive procedures are somewhat better rule-out tests, but are painful and present an infection risk. Furthermore, children are often sent to CT scans, the most commonly used procedures, when they present to the emergency room (ER) and such repeat exposure to radiation may be harmful.

Therefore, there remains a simple and reliable method for determining CSF shunt flow rates that can be interpreted by neurosurgeons and non-neurosurgeons with equal confidence.

All references cited herein are incorporated herein by reference in their entireties.

BRIEF SUMMARY OF THE INVENTION

An apparatus is disclosed for generating flow of cerebrospinal fluid (CSF) in an implanted CSF shunt having a shunt valve in symptomatic or asymptomatic patients. The apparatus comprises: a housing; a vibrating (e.g., reciprocating, pulsating, etc.) member disposed within the housing that generates a vibrating force when activated; and wherein the vibrating member generates pressure and flow of CSF within the CSF shunt when the vibrating member is placed against the skin and over the shunt valve and when the apparatus is energized to activate the shunt valve repeatedly.

A method is disclosed for generating flow of cerebrospinal fluid (CSF) in an implanted CSF shunt having a shunt valve in symptomatic or asymptomatic patients. The method comprises: applying a displaceable member, disposed within a housing, against the skin over the shunt valve; and activating the displaceable member to vibrate or pulsate the shunt valve repeatedly in order to generate pressure and flow of CSF within the CSF shunt.

An apparatus is disclosed for detecting the degree of occlusion in an implanted cerebrospinal fluid (CSF) shunt having a shunt valve in symptomatic or asymptomatic, said apparatus comprising: a pad that is placed against the skin of a patient over the location of the CSF shunt, wherein the pad comprises a plurality of temperature sensors that are aligned in a first direction and wherein one of the plurality of temperature sensors is aligned with the CSF shunt, each of the temperature sensors generating respective temperature data; a vibrating (e.g., reciprocating, pulsating, etc.) device that applies pulsation energy against the shunt valve for a predetermined period when the vibrating device is positioned against the skin over the shunt valve; and a sensor processing device that is electrically coupled to the pad for receiving temperature data from each of said temperature sensors, said sensor processing device using said temperature data to determine the degree of occlusion of said CSF shunt when a temperature source is applied to said pad for said predetermined period of time.

A method is disclosed for detecting the degree of occlusion in an implanted cerebrospinal fluid (CSF) shunt having a shunt valve in symptomatic or asymptomatic patients, wherein the method comprises: applying a plurality of temperature sensors against the skin over the location of the CSF shunt and aligned in a first direction, and wherein only one of the plurality of temperature sensors is aligned with the CSF shunt; applying a temperature source over the CSF shunt and upstream of the plurality of temperature sensors for a predetermined period; applying a vibrating (e.g., reciprocating, pulsating, etc.) device against the skin positioned over the shunt valve for applying a pulsation procedure for the predetermined period of time; collecting temperature data from the plurality of temperature sensors during said predetermined period of time; determining the degree of occlusion in said CSF shunt based on said collected data.

A method is disclosed for tracking shunt resistance in order to detect possible cerebrospinal fluid (CSF) shunt obstruction in a CSF shunt, having a shunt valve, implanted within a patient, wherein the method comprises: applying a plurality of temperature sensors against the skin over the location of the CSF shunt and aligned in a first direction, and wherein only one of the plurality of temperature sensors is aligned with the CSF shunt; applying a temperature source over the CSF shunt and upstream of the plurality of temperature sensors for a predetermined period; applying a vibrating (e.g., reciprocating, pulsating, etc.) device against the skin positioned over the shunt valve for applying a pulsation procedure for the predetermined period of time; collecting temperature data from the plurality of temperature sensors during the predetermined period of time; identifying a maximum temperature drop; and comparing the maximum temperature drop to a look up table that correlates shunt resistance therewith.

BRIEF DESCRIPTION OF SEVERAL VIEWS OF THE DRAWINGS

The invention will be described in conjunction with the following drawings in which like reference numerals designate like elements and wherein:

FIG. 1A is a functional block diagram of the reverse side (i.e., side applied against the skin of the patient) of the CSF ESPA portion of the present invention;

FIG. 1C is an isometric view of the measurement pad portion of the CSF ESPA using an insulation housing that encloses an ice source, e.g., an ice cube, for providing a temperature source;

DETAILED DESCRIPTION OF THE INVENTION

The invention of the present application is a micro-pumper 100 device that can be used as part of a cerebrospinal fluid (CSF) evaluation system 22 or it can be used as a stand-alone device for moving CSF. Thus, it should be understood that when used a part of a CSF evaluation system, the micro-pumper 100 is not limited to any one CSF evaluation system and that those CSF evaluation systems disclosed herein are by way of example only.

Figure 1:
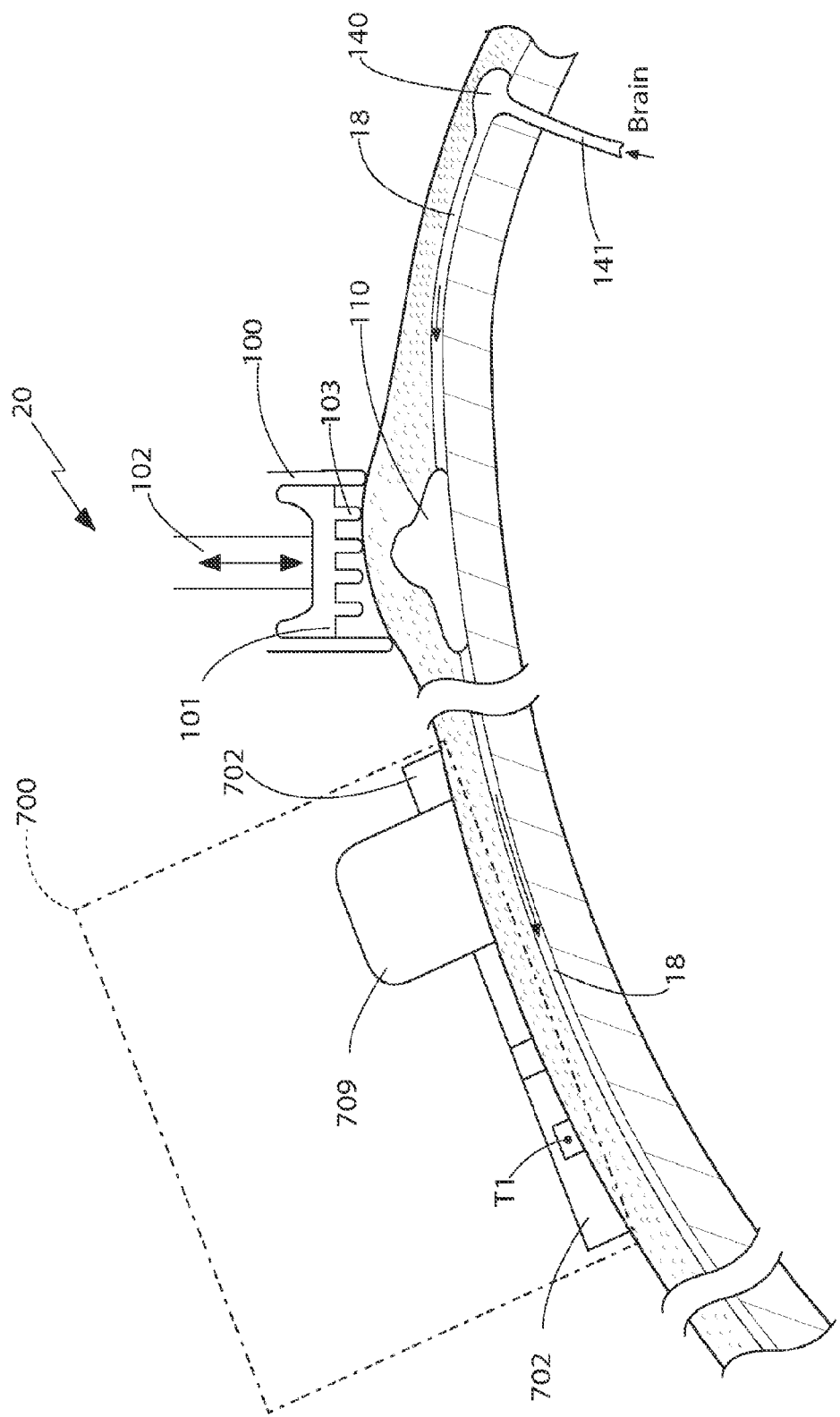
FIG. 1 is a partial illustration shown in section of the micro-pumper device of the present invention disposed over the CSF shunt valve dome under skin of a patient and being used in conjunction with an exemplary CSF flow evaluation system, also referred to as "ShuntCheck" thermo dilution flow detector (also referred to as "CSF ESPA")

As will be discussed in detail later, the micro-pumper 100 generates pressure within the CSF in the CSF shunt which in turn causes flow of CSF. The micro-pumper 100 is able to generate a plurality of small pressure spikes (also referred to as "gentle vibrations") in the CSF within the CSF shunt without creating large negative pressures (i.e., suction) at the CSF shunt tip, located within the brain of the patient. In particular, as shown in FIG. 1, the micro-pumper 100 is positioned against the skin over the dome portion of the CSF shunt valve. When the micro-pumper 100 is activated, the shunt valve 110 is gently cycled with a plurality of pressure spikes that create pressure within the CSF shunt to cause CSF flow while at the same time avoiding large negative pressures at the tip 141 of the shunt 18 disposed within the brain. In contrast, the current method of activating the shunt valve dome 110 is by having a person manually depress the valve with his/her fingers. The disadvantage of this method is that the operator creates undersirably large negative pressures at the tip 141 because the shunt valve dome is being strongly depressed at a very low frequency by the person. The micro-pumper 100 avoids these problems with its high frequency, low amplitude activation force on the shunt valve dome 110. As a result, the micro-pumper 100 can be used by itself to simply cause CSF flow in the shunt 18, thereby relieving pressure and while doing it safely.

An Exemplary CSF Evaluation System Using the Micro-Pumper 100

When used with a CSF shunt evaluation system 700, the micro-pumper device 100 along with the CSF shunt evaluation system 700 form an invention 20 of the present application. By way of example only, an exemplary CSF shunt evaluation system 700 comprises a CSF evaluation system pad and analyzer (hereinafter referred to as "CSF ESPA 700" and also referred to as "Shunt Check" or "Shunt Check thermo dilution flow detector").

It should be understood that other CSF shunt evaluation systems can be used such as those involving radionuclides.

The method of the present invention is a reliable method for detecting fluid flow and assessing flow rate in a subcutaneous CSF shunt.

The ability of the CSF ESPA 700 of the present invention 20 to detect no, low, or normal shunt flow was tested in an animal model and presented to the FDA in support of a 510(k) submission (cleared, May 2008). Briefly, the animal model incorporated a subcutaneous shunt through which warmed fluid was flowed at known rates using a positive-pressure pump, and the ability of the apparatus to detect flow, or the absence of flow was determined by blinded operators. Test results showed that multiple operators (including neurosurgeons and nurses) were able to detect the absence of flow in every test (100% sensitivity) when fluid was flowing at clinically-abnormal rates (0 to 5 ml/hour) through the shunt. The apparatus correctly detected the presence of flow with an accuracy (specificity) that was flow-rate dependent, varying from 70% (at 7.5 ml/h) to 100% (at 20 ml/h). At a flow rate of 10 ml/h, that approximates physiological CSF flow [28], the present invention exhibited a 92% accuracy (specificity) in detecting the presence of flow.

Additionally, the animal model results show that the present invention's temperature change data is an indicator of flow rate. As flow rate increases, the temperature drop recorded by the apparatus increases. As FIG. 5 indicates, this correlation is linear:

These results suggest that the CSF ESPA 700 should have a very high sensitivity, high specificity and a very high negative predictive value compared to current shunt test procedures (CT Scan, Shunt Tap and Shunt Series; see Table 1 above), which are only useful clinical symptoms that are at an advanced stage. Growing concern about radiation build-up due to frequent CT scans and the lack of a strong rule-out test for shunt failure, suggest that the CSF ESPA 700 will be increasingly adopted for assessing shunt function in hydrocephalus patients, especially in the presence of symptoms of shunt failure.

To meet the need for rapid and sensitive methods for determining shunt function, the CSF ESPA 700 allows non-invasive detection of cerebrospinal fluid flow through subcutaneous shunts. As discussed in detail below, the CSF ESPA 700 uses thermal convection technology-detecting a transcutaneous change in temperature as cooled cerebrospinal fluid flows through the subcutaneous portion of a ventriculoperitoneal shunt.

The CSF ESPA 700 comprises a single use disposable thermosensor which is placed on the skin over a subcutaneous shunt and a PDA based handheld device (the BioDisplay), also referred to as the CSF analyzer 704, which analyzes temperature data from the thermosensor and provides a time-temperature graph and a flow or no-flow result. The thermosensor is adhesively placed on the skin where the shunt crosses the clavicle. Ice is placed on the skin, "upstream" of the CSF flow from a thermosensor, to cool the CSF in the shunt. Thermosensors placed over the shunt detect the change in temperature as cooled fluid flows beneath them. The presence of flowing fluid is interpreted as a decrease in temperature detected by the thermosensors, while no change in temperature indicates the absence of flow.

Figure 5:
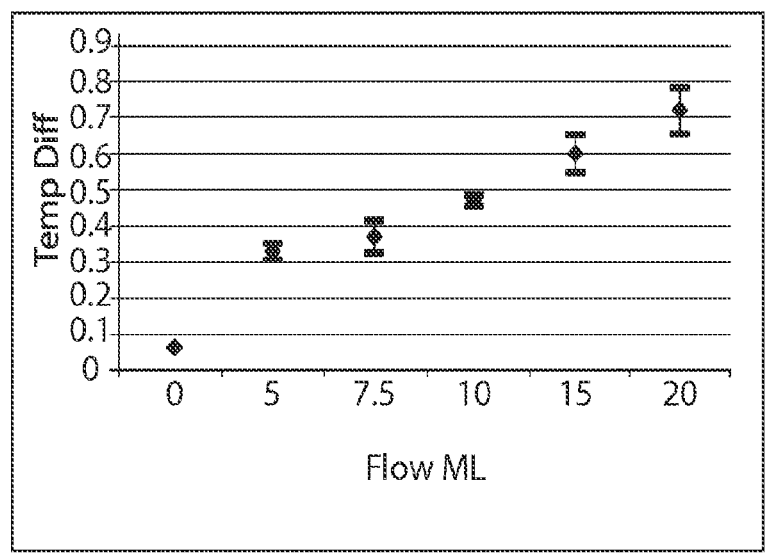
FIG. 5 is an illustration showing a temperature drop vs flow rate typical for the ShuntCheck thermo-dilution method and wherein the recorded temperature change is linearly correlated with flow rate through a subcutaneous shunt.

The CSF ESPA 700 was tested using an animal model of shunt flow and demonstrated 100% sensitivity (ability to accurately detect no-flow) and 92% specificity (ability to accurately detect flow). Additionally, the animal model experiments indicated that the CSF ESPA 700 can assess the rate of CSF fluid flow through shunts (FIG. 5). The temperature drop recorded by the CSF ESPA 700 varies linearly with flow rate—the deeper the temperature drop, the faster the flow. The FDA reviewed these animal model data and approved a 510(k) application for a first generation of the CSF ESPA 700 (K080168, approved May, 2008) as an aid to the detection of flow in implanted cerebrospinal fluid (CSF) shunts.

Early Human Clinical Studies Using the CSF ESPA 700 Indicate Intermittent CSF Flow Test results using the CSF ESPA 700 with pediatric hydrocephalus patients have been systematically evaluated. CSF ESPA 700 tests were conducted on patients who were independently classified as: 1) asymptomatic patients with patent shunts (n=36), 2) symptomatic patients with full or partial shunt patency (n=15), and 3) symptomatic patients with obstruction (n=3). It should be noted that asymptomatic patients presented for routine examination, and were all classified as being "without shunt obstruction" on the basis that none returned to the clinic with signs of obstruction within 1 week of ShuntCheck testing; Symptomatic patients presented for evaluation of clinical signs consistent with shunt obstruction, and were classified as "with shunt obstruction" or "without shunt obstruction" on the basis of the collective use/occurrence of other diagnostic tests (including CT scan), resolution of clinical signs, and/or direct assessment of the shunt catheter during revision surgery. The CSF ESPA 700 correctly identified all patients with obstruction (100% sensitivity), in agreement with its performance in the animal model. However, the CSF ESPA 700 showed "flow" results in only 50% of the patients (either symptomatic or asymptomatic) with patent shunts. This finding is consistent with previous studies of pediatric hydrocephalus patients [39] which show that CSF flow through shunts is intermittent. Drake [39] shows periods of no-flow of 30 to 40 minutes in duration followed by similar periods of flow. This is due to shunt valve design. When CSF levels in the ventricles are normal, shunt valves close and halt shunt flow to prevent over-drainage of CSF. It should be noted that intermittent CSF flow is likely to be a limiting factor on specificity performance of any method in which shunt patency or obstruction is being inferred from fluid flow measurements.

Thus, the present invention 20 provides a device and method which overcomes the disadvantages of the prior art by providing a CSF pumping method suitable for CSF VP (ventricular-atrial) and VA (ventricular-peritoneal) shunts while providing a shunt patency and resistance assessment method.

As mentioned previously, the invention 20 of the present application comprises a CSF evaluation system pad and analyzer (hereinafter referred to as "CSF ESPA 700") and a micro-pumper device 100, as shown in FIG. 1.

Figure 1B:
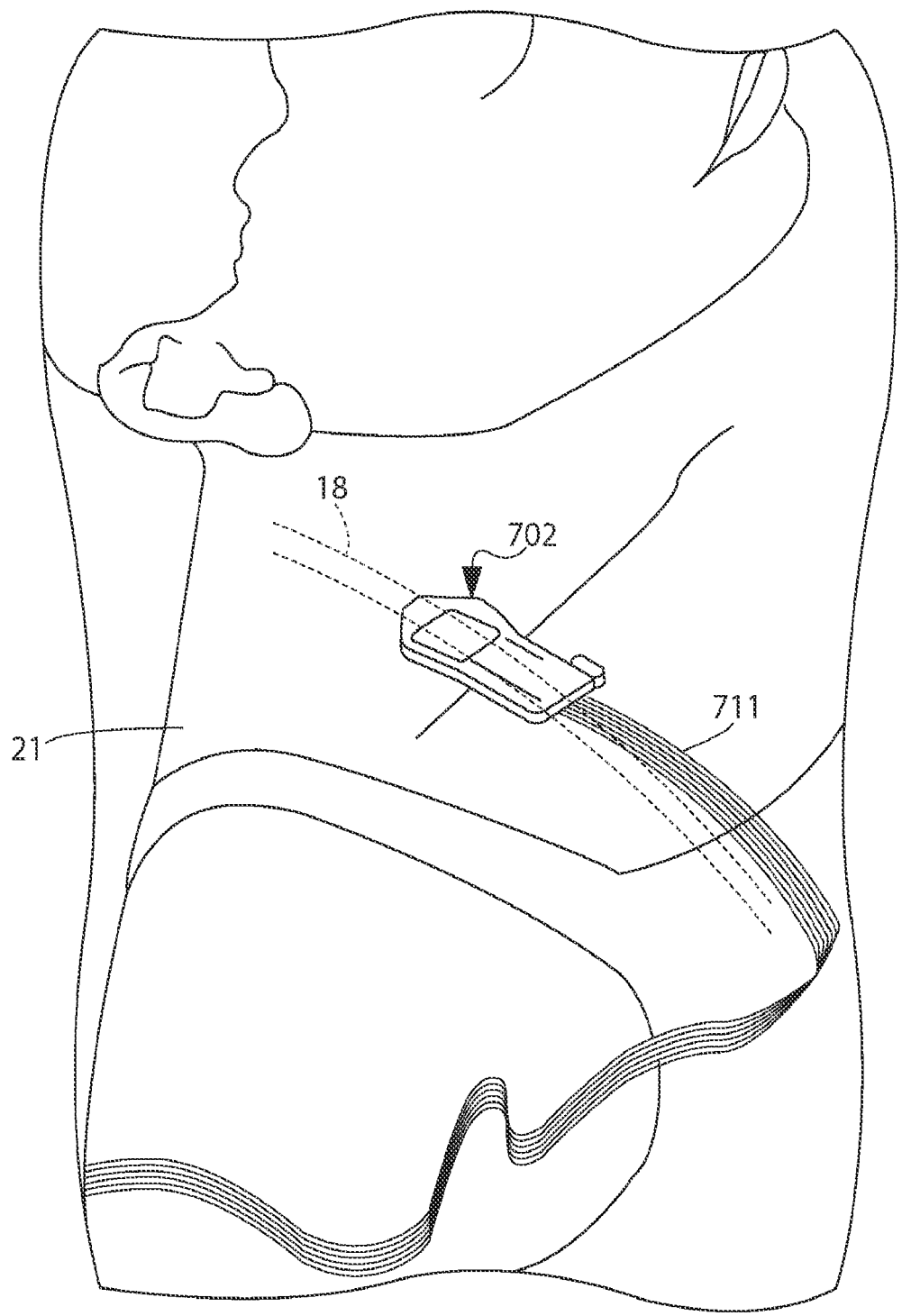
FIG. 1B shows how the measurement pad portion of the CSF ESPA is placed on the patient's skin while being located over the shunt tube (shown in phantom) beneath the skin and electrically coupled to the CSF analyzer portion of the CSF ESPA.

In particular, as shown most clearly in FIGS. 1A-1C, the CSF ESPA 700 comprises a thermal flow measurement pad 702 which is in electrical communication (e.g., via electrical cables 711 and connectors 712/714) with a CSF analyzer 704, also known as a sensor processing device (e.g., a processor with I/O). The measurement pad 702 comprises a plurality of sensors, such as thermistors, which are maintained in the correct relative geometries by the measurement pad 702. The analyzer 704 also provides the sensor excitation. The measurement pad 702 of the present invention is provided with at least one clear window 708 in order to permit accurate placement of the measurement pad 702 and the uniform application of a temperature source, e.g., a cooling means such as an ice cube or pack 10 (FIG. 1C). It is preferable to use a "plastic ice" cube (which contains water) which avoids or minimizes leaking when compared to an ice cube. To use this embodiment of the measurement pad 702, a shunt tube 18 which is positioned below the patient's skin 21 can be located by the physician and the patient's skin can be marked with a pen or other marking device in order to indicate the location of the shunt tube 18, typically over the clavicle, as shown in FIG. 1B. The measurement pad 702 comprises three temperature sensors (e.g., thermistors), T1, T2 and T3, as shown in FIG. 1A. When the measurement pad 702 is placed properly on the skin 21 and aligned with the shunt tube 18 located under the skin 21, the first temperature sensor T1 is aligned with the shunt tube's axis 18'. Temperature sensors T2 and T3 act as control temperature sensors and are aligned laterally, on opposite sides, with temperature sensor T1, as shown in FIG. 1A. In particular, it has been determined that human skin transfers heat and cold in a non-homogenous manner. By using only the shunt-aligned temperature sensor T1 and a single control temperature sensor T2, when the temperature source, e.g., a cooling means such as an ice cube or pack is placed on the measurement pad 702, the sensor T1 and the control sensor T2 experience different amounts of coldness. As a result, the temperature changes will not be equal even if there is no flow in the shunt 18. To overcome this problem, the CSF ESPA 700 includes another control sensor T3 on the other side of the shunt 18, thereby establishing two control sensors T2 and T3, symmetrically positioned on both sides of the shunt, as indicated by the distance S1. By way of example only, the distance S1 is approximately 8 mm from the shunt-aligned sensor T1. Also, each of the temperature sensors T1, T2 and T3 are positioned a distance S2 from the edge of the window 708. By way of example only, the distance S2 is approximately 8 mm. The insulation housing or enclosure 709 comprises a cube form that covers insulates the ice cube 10 in all directions except along the bottom surface which is open to permit direct contact with the skin 21 through the window 708. This permits the controlled application of a temperature "pulse" or "spike" or "wave" only at the skin surface 21 over the shunt 18. Without the insulated enclosure or housing 709, the "cold wave" generated by the ice cube 10 generates a fair amount of noise/inaccuracy that would be experienced by the sensors T1, T2 and T3 through the air. It should be noted that the cube form of the enclosure/housing 709 is by way of example only and that it may take on any shape to enclose or house the temperature source, whatever its shape, to prevent the transfer of the temperature pulse, wave or spike through the air but rather permit transfer only through an opening in the enclosure/housing that is in contact with the skin 21. It should be understood that the type of thermistor used for the temperature sensors T1, T2 and T3 must be fast response thermistors, i.e., a time constant of <5 seconds. This is important because the thermistor must be able to track the actual temperature without an appreciable time lag. By way of example only, the thermistors T1, T2 and T3 in the measurement pad 702 may comprise the MA100 Catheter Assembly which has a thermal response time in still water of 2.0 seconds. Another exemplary thermistor is the GE NTC thermistor. It should be noted that U.S. application Ser. No. 12/936,162 filed Oct. 1, 2010, entitled "Cerebrospinal Fluid Evaluation System Having Thermal Flow and Flow Rate Measurement Pad Using a Plurality of Control Sensors" is incorporated by reference in its entirety herein.

The micro-pumper device 100 is a portable, non-invasive tool which improves the diagnostic accuracy of kinetic shunt patency testing, including radionuclide studies or CSF ESPA 700 thermo-dilutions test, in pediatric hydrocephalus patients. CSF ESPA 700 is increasingly being adopted in the clinic as a front-line method for assessing CSF shunt function in routine check-ups, and in the emergency room. However, while the detection of fluid flow through the shunt, using the CSF ESPA 700 and other dynamic measures of fluid flow, confirms shunt patency (i.e., they exhibit high sensitivity), the absence of flow in any one test may not indicate obstruction (i.e., they exhibit poor specificity) since CSF flow can be naturally intermittent. Therefore, what is needed is a dynamic technique for evaluating fluid flow through CSF shunts that has high sensitivity and high specificity. There are currently no tools for differentiating between intermittently-flowing (patent) shunts and occluded shunts.

Shunt Pumping and "Micro-Pumping" to Address Intermittent Flow

With these findings in hand, Applicants have developed a method for combining shunt pumping (manually depressing the flushing mechanism in the shunt valve which generates a rush of CSF) with the CSF ESPA 700 test. This method has been tested in a bench model of CSF flow and validated it in an animal model. The method differentiated between patent shunts—which showed very significant temperature dips, indicative of strong CSF flow, totally occluded shunts—which showed no temperature dips, and partially occluded shunts—which showed restricted temperature dips.

To address an issue that shunt pumping may cause occlusion in certain circumstance due to suction at the proximal end of the shunt—as the flushing chamber of the shunt refills after pumping, Applicants developed the micro-pumper 100, a miniature, non-invasive device (see FIGS. 1, 2 and 3) which is held against the shunt valve (which is typically implanted under the scalp behind the ear) and which provides a specific vibration pulse to the valve. The vibration pulses act like manual shunt pumping in miniature and generate a controlled and reproducible level of flow through the valve. Importantly, micro-pumping generates several times less negative pressure in the proximal catheter than manual pumping.

Working with two popular CSF shunt valves, the Integra DP Standard System and the Sophysa Polaris SPVA programmable valve, a variety of pulse generators, pulse amplitudes and pulse frequency/duration patterns were tested. A commercially-available miniature vibrating motor was selected and a pulse amplitude/frequency/duration pattern was developed which generates 20 ml/hr of CSF shunt flow in patent shunts (the normal steady state production of CSF in humans). In partially obstructed shunts, the micro-pumper 100 generates a restricted level of flow (restricted by the level of obstruction). In totally occluded shunts, the micro-pumper 100 generates no flow.

CSF ESPA 700 bench tests of micro-pumped patent shunts show >1° C. of temperature drop—consistent with 20 ml/hr flow. Totally occluded shunts show no temperature drop. Partial occlusion shows restricted temperature drop. This means that the combination of the micro-pumper 100 and the CSF ESPA 700 provides an accurate test for shunt patency.

Innovation and Significance to Human Health

The innovation of the present invention 20 is the development of a new tool and clinical method for the diagnosis and early diagnosis of CSF shunt malfunction in hydrocephalus patients presenting to the ED with symptoms consistent with shunt obstruction. Up to 30% of mortalities in shunted patients are attributed to shunt malfunction and there are currently no non-invasive techniques that can reliably be used as stand-alone diagnostic instruments for shunt obstruction. The micro-pumper device 100 can rapidly (e.g., within 5 minutes) determine shunt patency. Its portability, ease of use, safety, and relative inexpensiveness enable it to be used routinely in emergency departments and in neurosurgical clinical settings.

There are currently 300,000 people in the U.S. with CSF shunts. Approximately 30,000 shunt revision surgeries are conducted annually in the U.S. Each year 120,000 patients present with symptoms of shunt failure to hospital emergency rooms—primarily to the 453 level I and II emergency rooms in the U.S. Strong sensitivity and specificity results demonstrated in the clinical study combined with the device's non-invasive procedure ideally make the CSF ESPA 700 thermo dilution method and CSF ESPA 700/micro-pumper device 100 combination the standard of care for symptomatic hydrocephalus patients and enables neurosurgeons and emergency medicine physicians to reduce the number of CT Scans conducted on "false alarm" symptomatic patients and thereby reduce the radiation build up caused by the scans.

Figure 6:
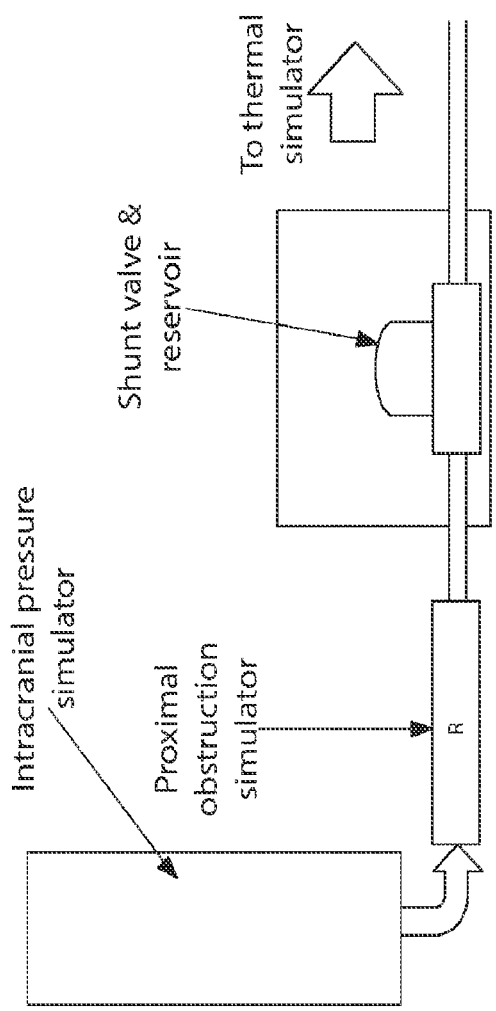
FIG. 6 is an illustration showing a bench-top setup used to test shunt patency.

Development of a Bench Top Model of Intermittent Flow and Shunt Patency or Obstruction Before developing tools to address intermittent CSF flow, a bench top model was developed which replicates shunt patency or obstruction and intermittent flow and which allows testing the CSF ESPA's 700 ability to differentiate between obstruction and intermittent flow. The model consists of two sections, a brain & CSF shunt hydraulics simulator and a thermal response simulator. The hydraulic simulator is depicted in FIG. 6:

The ICP (intracranial pressure) simulator is a water column which allows setting ICP at normal levels (5 to 15 mm Hg), elevated levels (20 to 30 mm Hg) or critical levels (>40 mm Hg).

Hydraulic resistors, comprising calibrated stainless steel needles, were placed at the tip of the proximal catheter (the most common site of obstruction in pediatric patients), and values set to 0 mmHg/ml/h (patent), 1 mmHg/ml/h (partial obstruction), and 2 mmHg/ml/h (critical obstruction). This definition was based on the following: 1) the average person produces 20 ml of CSF per hour [41,42]; 2) the highest ICP level before the patient loses consciousness is 40 mmHg [43]; and 3) relatively normal ICP pressure is less than 20 mmHg (normal ICP=10 mmHg, elevated=20 mmHg) [43-45]. In order to maintain constant ICP, CSF is typically removed from the ventricles at the same rate as it is produced. If a hydrocephalus patient is 100% shunt-dependent (a worst case scenario since most patients exhibit a combination of natural and shunt drainage), then under normal ICP (10 mmHg), the shunt needs to drain CSF at approximately 20 ml/h, equating to a hydraulic resistance in the shunt of 0.5 mmHg/ml/h. This is a low-resistance circumstance associated with a fully-patent shunt. As the shunt becomes increasingly obstructed, and hydraulic resistance increases to 1-2 mmHg/ml/h, ICP increases to 20-40 mmHg (assuming CSF must be removed at 20 ml/h). We can therefore classify shunts into three categories of patency or obstruction, based on their hydraulic resistance (r): patent (r<1), partial obstruction (1<r<2) and critically obstructed (r>2).

The third component is a shunt valve which consists of a fluid reservoir and a check valve. The reservoir can be pumped to flush the shunt. The check valve prevents backflow of CSF and closes when ICP is low, preventing over-drainage of the ventricles. Initial testing was conducted using popular shunt valves from Integra Life Sciences and Sophysa.

Figure 7:
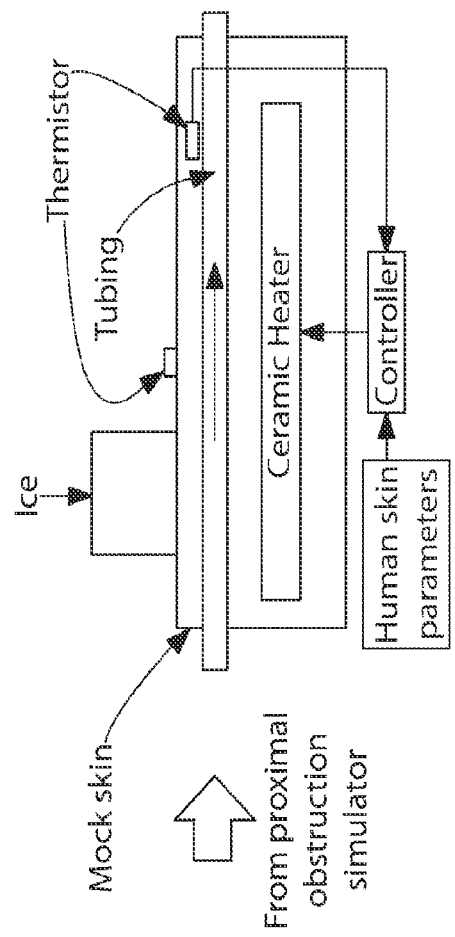
FIG. 7 is an illustration showing bench-top model used to study thermal effects related to CSF shunt flow.

The second section of the bench top model is a thermal simulator, enabling the performance of CSF ESPA 700 tests of patency. Since CSF ESPA 700 uses thermal convection (detection of cooled fluid through skin) to determine flow, an in vitro model, was developed and validated, that was capable of simulating the in vivo thermal responses to the CSF ESPA 700 test. The model consisted of a shunt system (proximal catheter, reservoir and shunt valve plus distal catheter); mock tissue (silicon rubber); ceramic heater, thermal sensor controlling mock tissue temperature, and temperature controller. The system is shown in FIG. 7.

The heater is controlled by closed-loop feedback in order to simulate the physiological responses to skin to exposure to cold.

Figure 8:
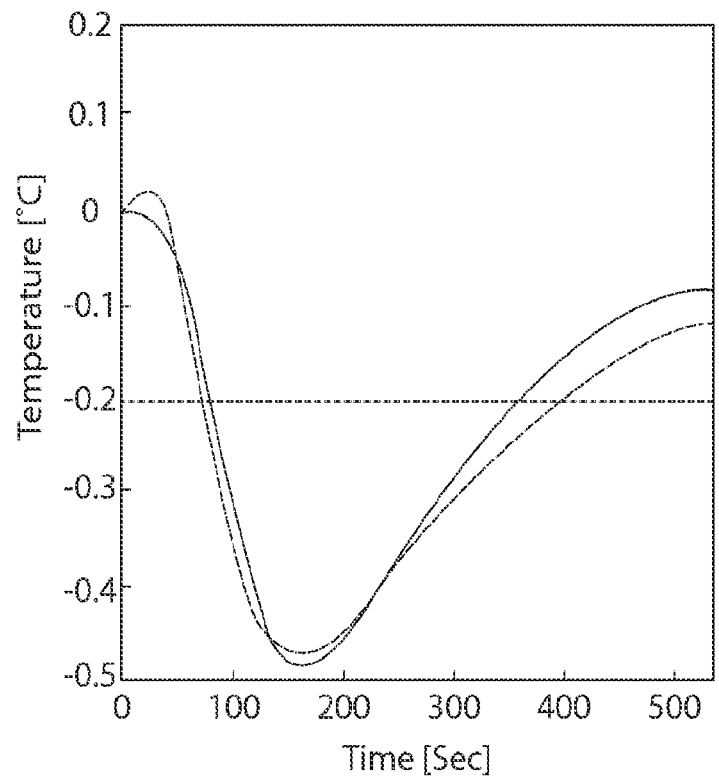
FIG. 8 is an illustration showing thermal response agreement between bench-top model and animal experiments.
Figure 9:
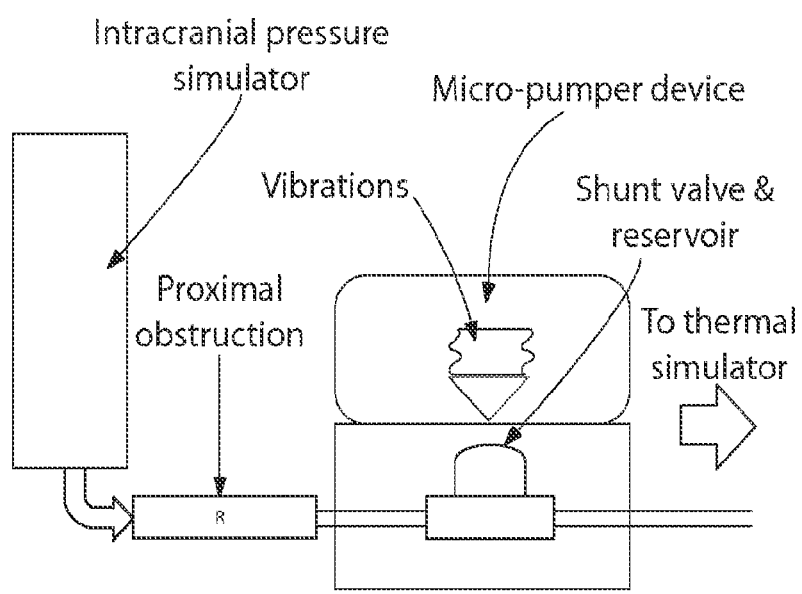
FIG. 9 is an illustration showing bench-top model used to study ShuntCheck thermo-dilution method in conjunction with ShuntCheck micro-pumper device.

The system was experimentally calibrated to responses recorded in porcine to closely approximate living skin's reaction to cold stimuli. FIG. 8 shows the calibration curves obtained in the living pig skin, and in the bench model. The curves are almost identical (<5% difference) on negative and positive slopes, the time for the minima is very similar (10 sec difference). This data shows that the bench model simulates accurately the thermal response of the porcine skin. In particular, FIG. 8 shows a calibration curve showing the thermal response to flow of 5 ml/h on both porcine skin and bench top setup; the green line (viz., the lighter line in black & white) represents the bench model response.

Figure 4:
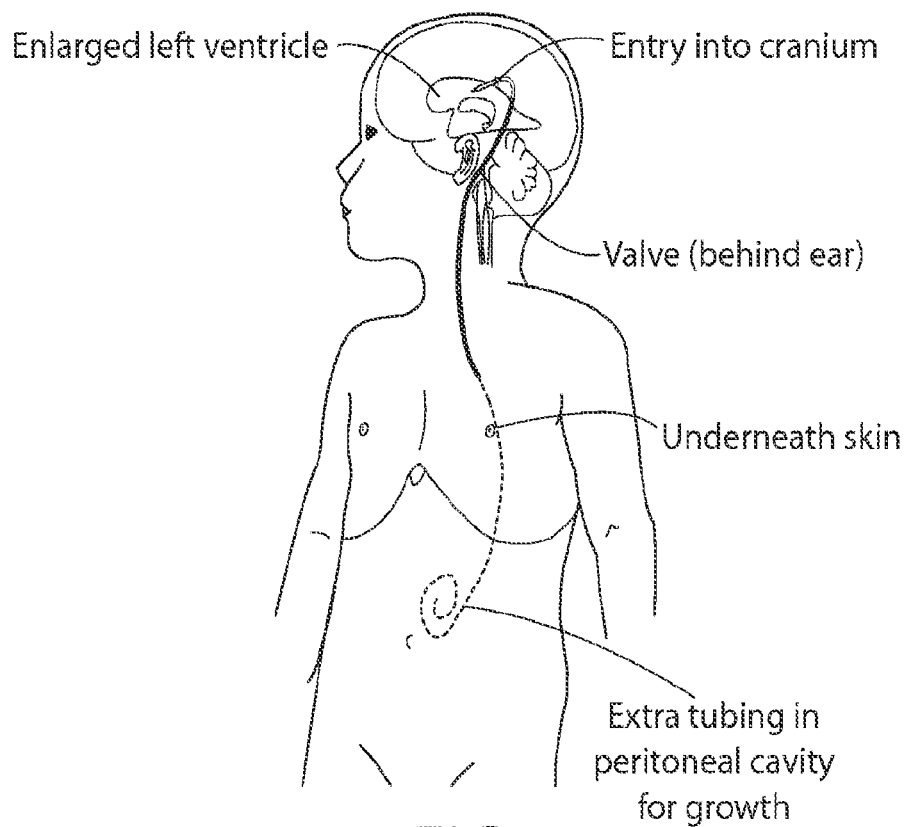
FIG. 4 is an illustration showing anatomy of a typical CSF VP shunt.

The experimental setup consist of the ICP simulator (hydraulic accumulator with compliance value dV/dP=0.2 through 0.14 ml/mmHg) proximal resistor connected to the proximal catheter of the shunt system, proximal catheter, shunt pumping device (reservoir), shunt valve, and distal catheter. The hydraulic output (distal catheter) is connected to the thermal simulator shown in FIG. 4 which mimics thermal behavior of skin.

Figure 10:
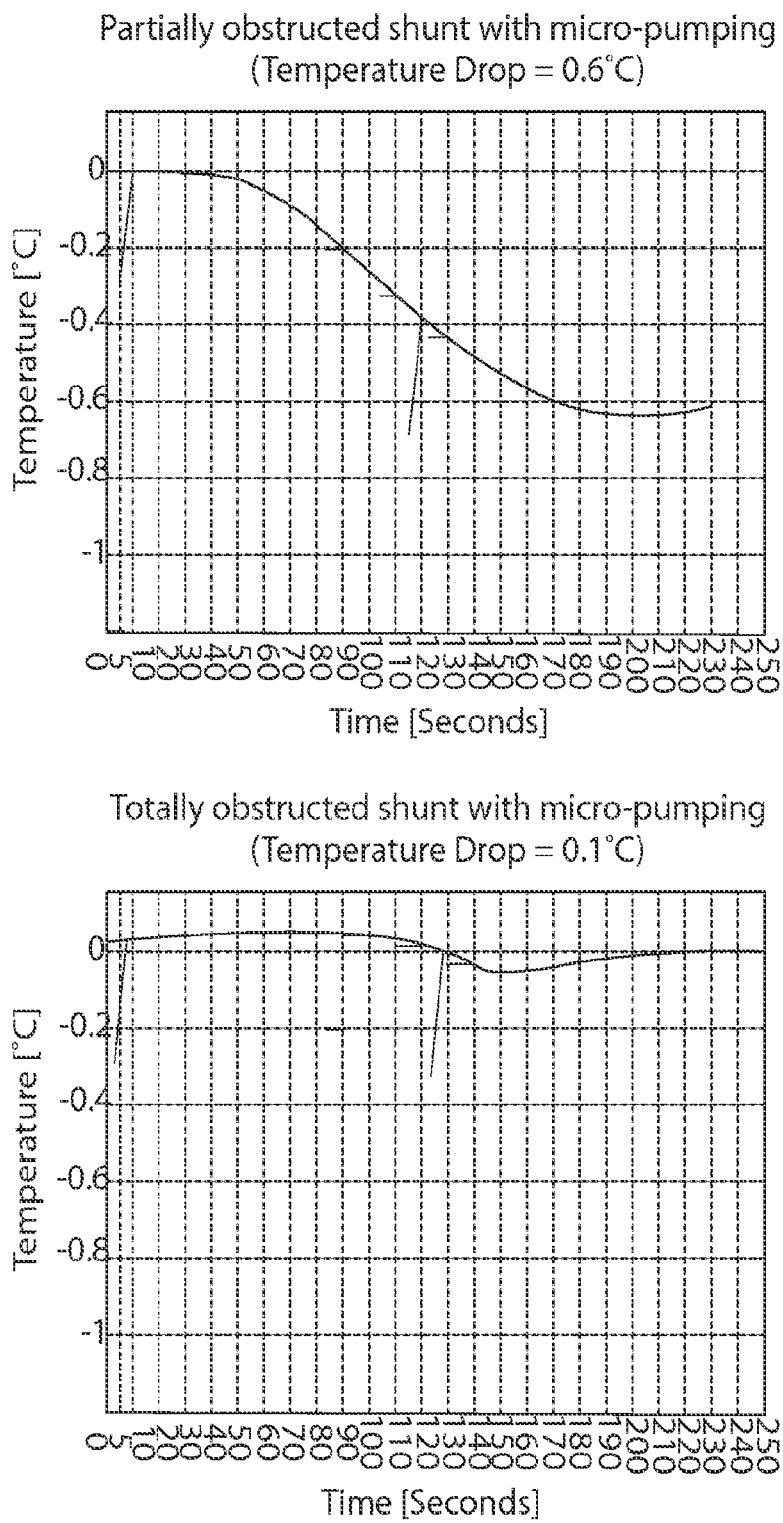
FIG. 10 is an illustration showing comparison between thermal responses obtained by ShuntCheck thermo-dilution in conjunction with ShuntCheck micro-pumper method on patent and obstructed shunt.
Figure 11:
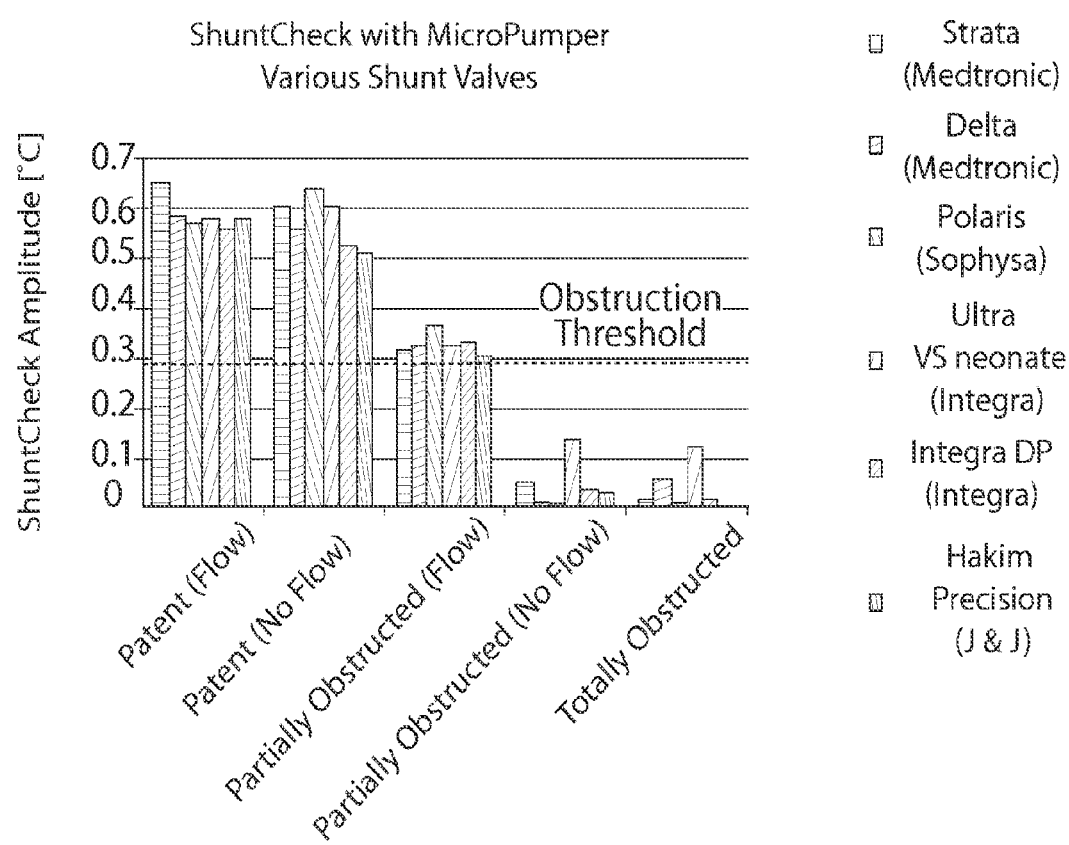
FIG. 11 is an illustration showing comparison between thermal responses (absolute temperature drops) obtained by ShuntCheck thermo-dilution in conjunction with Shunt-Check micro-pumper method on patent, partially obstructed and obstructed shunt. Results obtained on several types of CSF valves.

Proximal resistance is set consistent with patent, partially occluded or occluded and an initial flow is established by setting ICP in the ICP simulator. The ice cube is placed on the mock skin, the micro-pumper device 100 applied 3×10 second pulses of vibrations (f=120 Hz) directly to the valve, and the thermal response downstream of the ice cube is measured by the CSF ESPA sensor. Responses are recorded over 4 min periods and correlated with level of occlusion. Examples of thermal responses correlated with different levels of occlusion and initial flows are shown in FIGS. 10 and 11.

Patent shunts show >1.0° C. in the CSF temperature drop recorded by the CSF ESPA 700, indicative of robust fluid flow. In a flowing patent shunt, the temperature drop is steady and smooth. In an intermittently flowing patent shunt, cooling is delayed until the micro-pumper 100 activates (90 seconds into the test) and generates fluid flow. The temperature drops rapidly at that point.

These results show that the micro-pumper device 100 combined with the CSF ESPA 700 is capable of differentiating between patent shunts (flowing or temporarily non-flowing), partially occluded and totally occluded shunts. These findings suggest that the micro-pumper device 100 addresses the specificity problem identified in prior research, by differentiating between patent non-flowing shunts and totally occluded shunts. The ability to differentiate between patent and partially occluded shunts suggests that the CSF ESPA 700 and micro-pumper device 100 combination may also identify a failing shunt at an early stage of occlusion.

At this point in time, 20 CSF ESPA 700 and micro-pumper 100 patient tests have been conducted. 17 patients had patent shunts (were either asymptomatic or CT scans plus X-ray series indicated patency) and 3 had occluded shunts and revision surgery.

Micro-pumper device 100 safety and operator and patient satisfaction were confirmed. Patients found the Micro-Pumper to be pleasant. The operator thought the procedure was straightforward.

CSF ESPA 700 plus micro-pumper device 100 correctly identified all three shunt occlusions—for a 100% sensitivity The procedure correctly identified 9 of 17 patent shunts. In five false occlusion cases, it was discovered that the test operator pressed the micro-pumper device 100 firmly against the patients' scalps (an average of 1.2 Kg of pressure). Bench testing was run with light pressure (300 to 500 g pressure). Subsequent bench tested was conducted with firm vs light pressure and it was discovered that a number of valves (particularly Medtronic valves) flow poorly under firm pressure.

Figure 3:
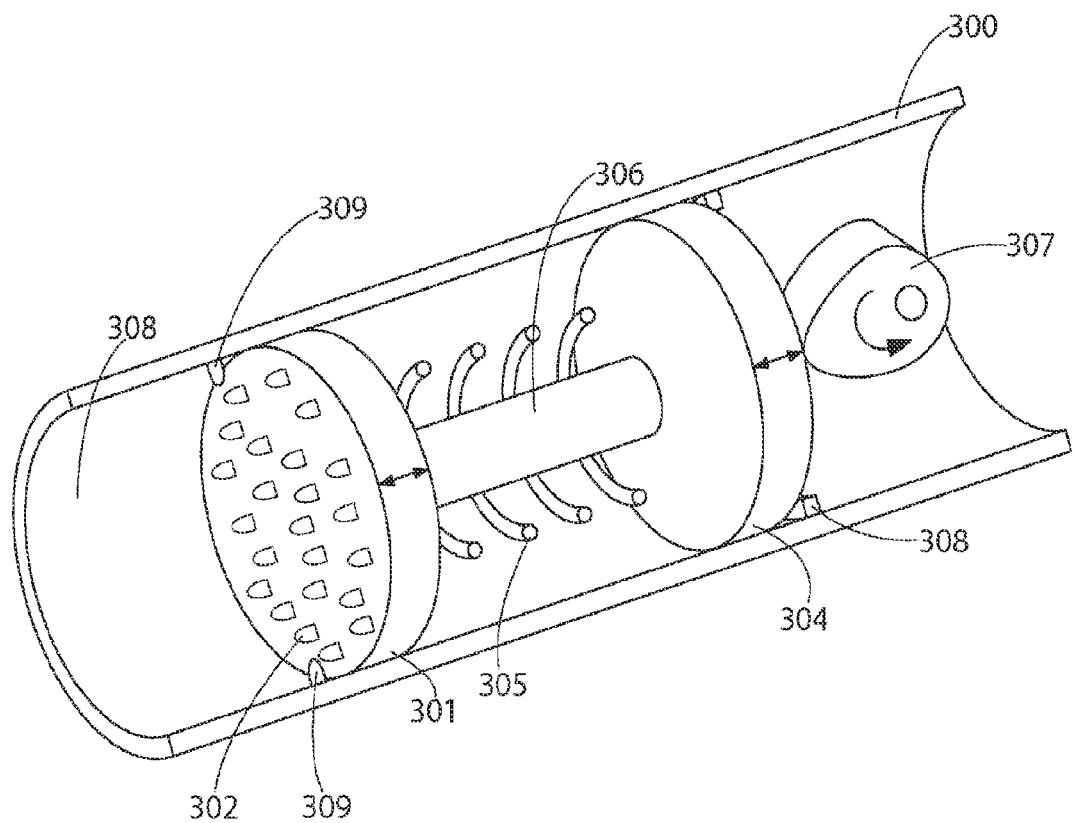
FIG. 3 is an enlarged isometric view, shown partially, of the ShuntCheck micro-pumper device.

As shown in FIG. 3, the preferred embodiment of the micro-pumper device 100 comprises a "floating foot" 301 which allows for the valve dome 110 (FIG. 1) or tubing 18 pre-stress. The operator applies certain pressure to the valve dome (or other part of the shunt system) by pushing the floating foot against the skin surface. This action compresses the spring and by doing so provides certain calibrated initial pressure (pre-stress) to the valve dome or other part of the shunt system. This setup allows for: 1) adjustment to different valve dome heights, and 2) breaks the spherical or cylindrical curvature of the valve dome or tubing (This action allows for less force to be used during the pulsation phase) 3) provides an uniform starting pressure on all valves.

The spring 305 placed between the foot 301 and floating piston 304 helps provide calibrated force to the valve or tubing during the pulsation phase and allow for constant force pulsation. The force from the motor is delivered to the valve via spring 305. In an alternative embodiment the force from the motor is delivered by a rigid link between the motor and the foot which allows for constant displacement pumping (each compression takes the same amount of displacement as oppose to constant force where each displacement is generated by a constant force.

The foot comprises "toes" 302. This feature assures that the pulsating pressure is delivered to the valve dome or shunt tubing even if the skin is covered with hair. The "toes" distribution is such that at least one toe is in contact with the valve dome. In the alternative embodiment the toes can be replaced by grooves, ridges, bumps or other structures protruding from the foot or carved in the foot.

It should be understood that the displaceable foot 301 may comprises a plurality of sections and wherein each section vibrates separately.

An alternative to the floating is a force gauge which measures the force which the test operator applies to the micro-pumper device 100 and which indicates by a visual or auditory signal that the force is too light, too heavy or in the correct range of >300 g and <1000 g.

The micro-pumper device 100 can be programmable in such a way that the pattern of pulsations (frequency, duty cycle, force, displacement and duration of pulsation periods) can be pre-programmed and memorized by the device, reprogrammed using external device or re-programmed/change using the micro-pumper's 100 controls. The pulsation patterns can be adjusted to obtain desired level of the CSF flow in the shunt system. By way of example only, the micro-pumper device 100 may comprise a microprocessor or microcontroller which is programmed to control motor operation or load cell to deliver the desired frequency, duty cycle, force, displacement and pulse duration/period.

The pulsation pattern can be adjusted according to the valve type or skin thickness or kept constant at the level optimal for the variety of valves and skin thicknesses.

The micro-pumper housing is shaped in such a way that it forms two reliefs to prevent the shunt tubing from being pinched off by the edges of the device (not shown).

Figure 12:
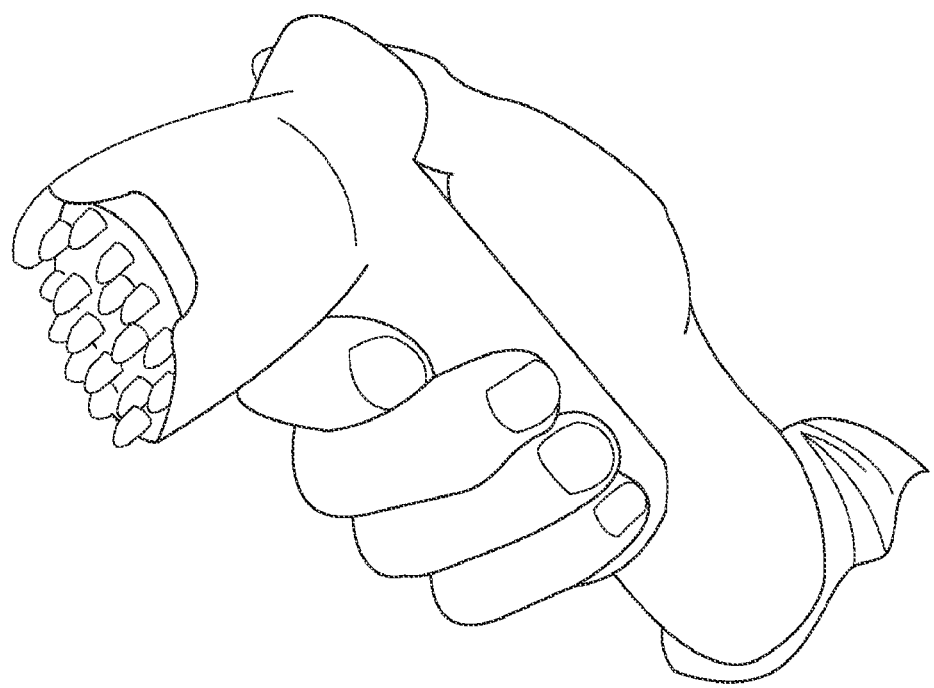
FIG. 12 is an illustration showing a preferred embodiment of the micro-pumper device wherein the main body (also referred to as "housing") forms an angle with the foot.
Figure 13:
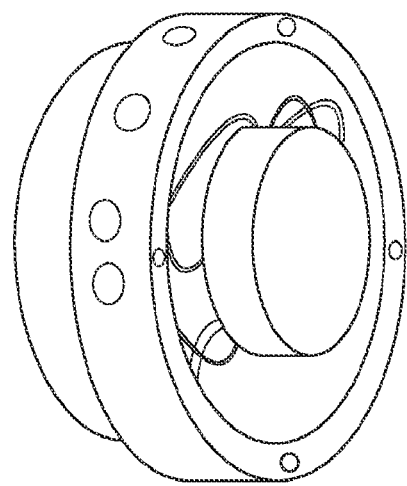
FIG. 13 is an illustration showing a preferred embodiment of the micro-pumper device wherein the main body is linked with the foot via an elastic membrane.

FIG. 3 shows the preferred embodiment of the micro-pumper device 100. The preferred embodiment consists of a main cylindrical body 300, which is also used as a handle, and foot 301 outfitted with short rods 302. The foot is supported by a shaft 306 rigidly connected to the foot, the shaft is inserted into a floating piston 304 in such a way that the rod and piston can move independently on a certain distance. It allows the foot to adjust its position to valves of different heights and keep relatively constant contact pressure between the skin surface and the foot. A spring 305 is placed between the piston and foot. The spring pushes the foot and the piston apart. The piston motion is partially restricted by a semi-partition 308 inside the cylindrical body. The foot motion is partially restricted by at least one rigid element 309 placed inside the main body cylinder 300. FIGS. 12 and 13 show prototypes of the micro-pumper device 100.

Figure 2:
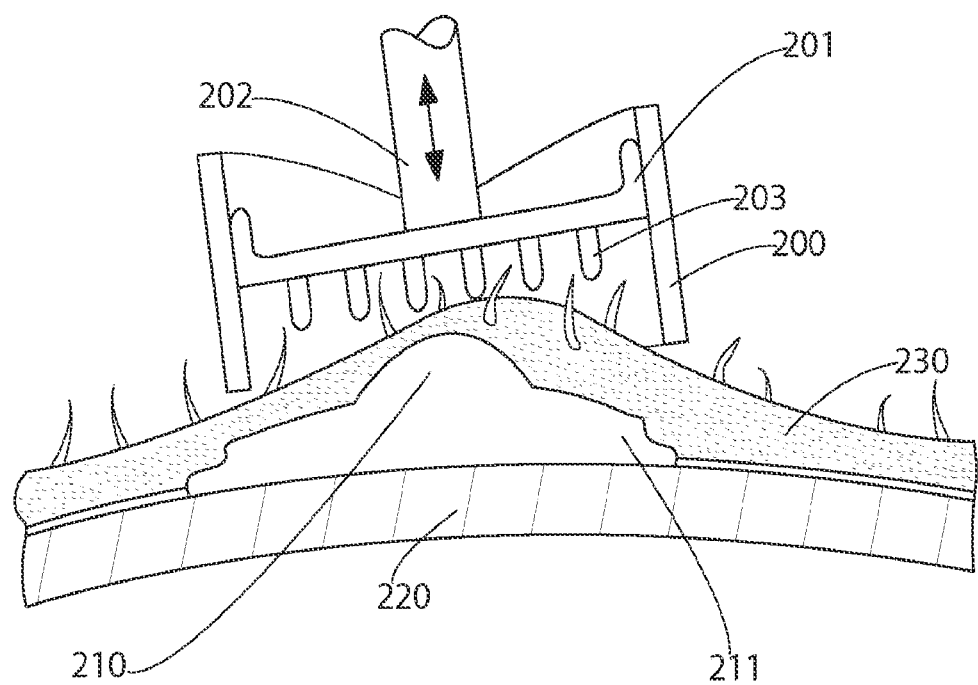
FIG. 2 is a sectional view of the micro-pumper placed on the skull over the CSF shunt valve dome.

In FIG. 2 the sectional view of the micro-pumper 100 placed over the valve dome is shown. Reference number 220 identifies the bone of the patient's skull. This configuration can be used to generate flow in the CSF shunt system as a safe alternative to manual pumping. The user holds the housing 200 of the micro-pumper 100 and orients the foot 202 against the skin over the shunt valve 210. The foot 202 outfitted with an array of short rods 203 compresses, in a periodic manner, the valve 210, implanted under the skin surface 230. As can be seen in FIG. 2, the foot 202 moves within the lower part of the housing 200 when activated. The CSF is pumped due to pressure generated in the dome 210. The pressure opens the CSF shunt system check valve (not shown) and generates flow.

The foot is placed over the valve dome (FIGS. 1 and 2). The dome pushes the foot inside the cylindrical body and initially compresses the spring 305. A cam 307 driven by a motor (e.g., an electric motor, not shown) pushes a floating piston. The floating piston compresses the spring 305. The spring pushes the foot 301 and by doing so transfers motion of the cam to the valve dome. The dome motion compresses CSF fluid inside the shunt system 210 and causes the CSF shunt system check valve (not shown) to open and move fluid to the abdominal cavity. Alternatively, the floating piston can be driven by a solenoid or by an electromagnetic head or by a pneumatic motor.

Figure 14:
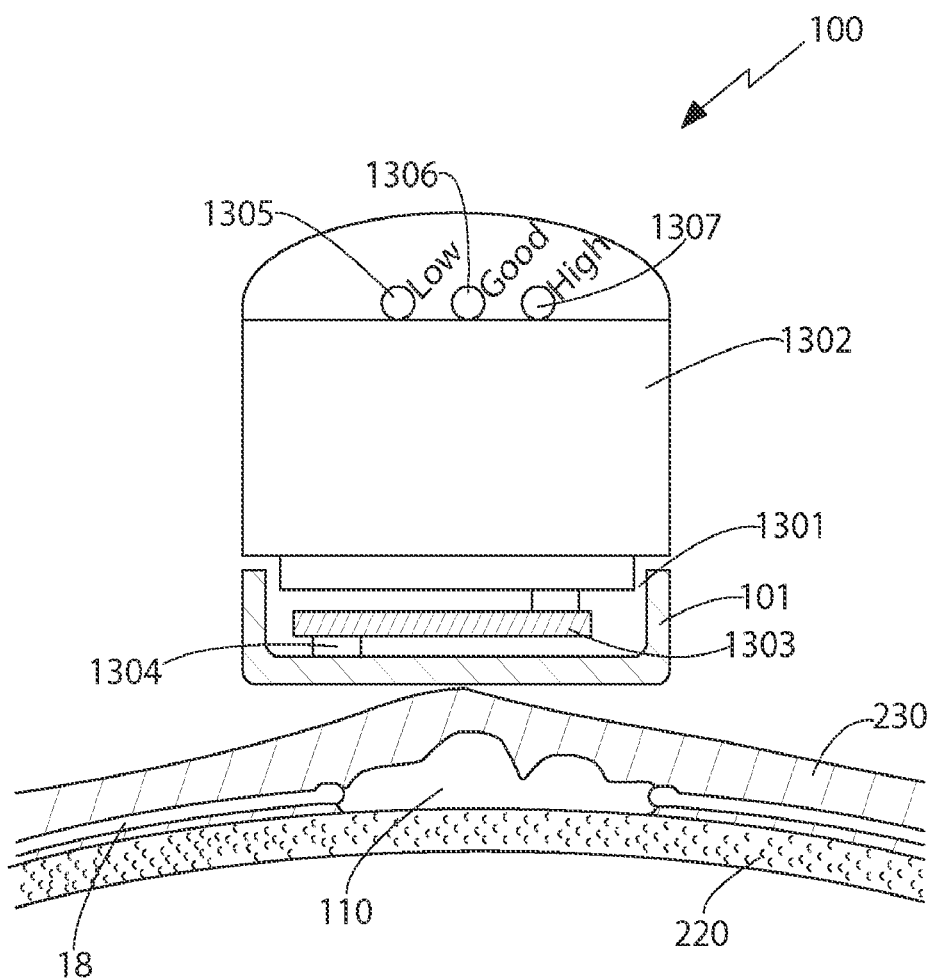
FIG. 14 is a sectional view of micro-pumper with a force gauge and LED lights which indicate the force of the micro-pumper against the scalp—low, good, high.

The alternative to floating foot design is the force gauge design shown in FIG. 14. The housing 1302 contains a motor (e.g., an electric motor) with a counterweight which generates the vibration power and contains the printed circuit board, batteries and the switch. A section of this enclosure (1301) slides into the foot 101. There is clearance between the foot and housing to allow free movement (no friction) for accurate force measurement. The foot 101 contains a load cell, a double beam cantilever with strain gauges, which is attached to the foot at 1304 and to the housing at 1303. When the test operator presses down on the housing, the force is measured by the load cell. The load cell provides a signal to an integrated circuit on the printed circuit board in the housing which categorizes the force as too light, acceptable or too heavy and activates one of three LED lights (1305, 1306 or 1307) to guide the operator to the correct level of force. Thus, in this version of the micro-pumper 100 the foot 101 is rigidly-linked with the overall device 100 such that the entire device vibrates.

The micro-pumper 100 can be used in conjunction with the CSF ESPA 700 thermo-dilution device (FIG. 1) in order to assess shunt patency. The micro-pumper device 100 pushes the dome110 via foot 101. As a result of this pumping action the CSF moves in the shunt 151 from brain to abdomen. The skin surface is cooled by an ice cube 120 and the temperature drop is measured by thermal sensor 132 placed over the shunt 151. The temperature drop amplitude measured by the thermosensor 132 can be correlated with the shunt system resistance (obstruction level). An example shown in FIG. 11.

It is a well established fact that as resistance to CSF outflow increases the intracranial pressure increases as well. For a given patient the amount of CSF produced in the ventricles per hour is roughly 20 ml. As the resistance to CSF flow reaches 7.5 [ml/mmHg] the intracranial pressure will reach 15 mmHg. For resistances of 15 [ml/mmHg] the ICP will reach 30 mmHg. The formula linking ICP to resistance and CSF flow is:

$ICP = R*F$ where $R$ is resistance and $F$ is CSF flow.
  ICP is intracranial pressure.

For shunted patients highly dependent on VP or VA shunts the R is roughly equal to the shunt system resistance. Thus, it is of critical importance to know the R, so the necessary steps (e.g. shunt revision) can be taken to avoid dangerous levels of ICP.

It would be even more beneficial if one could monitor R and warn if there is a trend of R increasing its value. The micro-pumper 100 in conjunction with CSF ESPA 700 thermo-dilution method can be used to assess shunt system hydraulic resistance, even if the resistance is low, and serve as a tracking system for hydraulic resistance changes.

Due to the fact that the micro-pumper device 100 generates relatively constant driving pressure (pressure pushing fluid through the check valve) one can utilize this to assess shunt resistance if the CSF flow is being measured simultaneously. As shown in FIG. 11 and the studies related thereto, the amount of flow generated by the micro-pumper device 100 under certain conditions is proportional to shunt resistance. It can be concluded that by using the micro-pumper device 100 and some CSF flow measurement method (e.g., ShuntCheck thermo-dilution or radionuclide method) one can assess shunt resistance to flow.

Seven different procedures to detect shunt patency are claimed.

1. Method of assessing full patency in symptomatic patients (low R)
2. Method of assessing partial occlusion symptomatic patients (medium R)
3. Method of assessing complete occlusion in symptomatic patients (R infinite)
4. Method of assessing full patency in asymptomatic patients (low R)
5. Method of assessing partial occlusion asymptomatic patients (medium R)
6. Method of assessing complete occlusion in asymptomatic patients (R infinite)
7. Method of tracking shunt resistance in order to early detect possible shunt obstruction.

An example of a shunt resistance assessment method in 5 steps is described below. This example is based on an observation that absolute flow rates generated by the micro-pumper device 100 correspond to specific shunt resistances:
1. The CSF ESPA sensor patch 702 is applied to the skin 21 as described in ShuntCheck manual;
2. The ice cube is applied to the skin as described in ShuntCheck manual;
3. The micro-pumper device 100 is applied to the shunt valve dome and the pulsation procedure is activated for a period of 30 sec to 2 minutes.
4. The temperature drop on the thermosensor 132 is measured or the entire procedure of ShuntCheck is executed as described in the ShuntCheck manual.
5. The maximum temperature drop is compared to the look up table and the corresponding shunt resistance is established.

Another example utilizes a different principle that is: the flow is generated with two different frequencies of pulsation, each frequency generating different pressure across the check valve. Pressure is proportional to frequency of pulsations, thus the ratio between those two pressures are then known (the absolute value does not have to be known). This fact can be described by a system of linear equations:

$$\mathrm{delta}P = R*F1$$

$$\mathrm{delta}P*\mathrm{constant} = R*F2$$

where deltaP is pressure across the check valve generated by lower frequency, R resistance, F1 flow recorded with the lower frequency and F2 flow recorded with the higher frequency. "Constant" is the known ratio of pressures (high frequency pressure to low frequency pressure). By running two tests with two different frequencies and known ratio of pressures generated across the check valve, one can measure F1 and F2 and solve the system of equations for deltaP and R.

Yet another example of the shunt resistance assessment method would be to observe the flow rates generated by the micro-pumper device 100 in the time domain and from flow rate changes assess the shunt resistance. The steps of this method are:
1. The ShuntCheck sensor patch 702 is applied to the skin as described in ShuntCheck manual.
2. The ice cube is applied to the skin as described in ShuntCheck manual.
3. The micro-pumper device 100 is applied to the shunt valve dome and the pulsation procedure is activated for a period of several seconds then the micro-pumper device 100 is turned off for 30 sec to 2 minutes. This step is repeated several times.
4. The temperature drop on the thermosensor T2 is recorded over several minutes.
5. The temperature gradients T/t are measured during "on" and "off" periods. The values are compared to the look up table and the corresponding shunt resistance is established. In this case the look up table links gradients T/t (Temperature over time) to shunt resistance.

In shunt dependent patients, after the shunt resistance assessment, if the natural flow is present, (flow due to certain ICP) the ShuntCheck flow measurement can be used to calculate the ICP level using equation:

$$ICP = R*F$$

In patients partially dependent on shunts, if the shunt resistance, shunt flow and ICP are known (e.g. ICP is measured by Camino), the percentage of shunt dependency can be assessed by calculating natural resistance RN to CSF outflow by solving equation:

$$ICP = F*(RN+R)/RN*R \text{ for } RN$$

100*RN/(RN+R) yields a percentage of shunt dependency.

While the invention has been described in detail and with reference to specific examples thereof, it will be apparent to one skilled in the art that various changes and modifications can be made therein without departing from the spirit and scope thereof.

References Cited
1. Bondurant, C. and D. Jiminez, Epidemiology of cerebrospinal fluid shunting. Pediatr Neurosurg, 1995. 23: p. 254-258.
2. Bech-Azeddine, R., et al., Idiopathic normal-pressure hydrocephalus: evaluation and findings in a multidisciplinary memory clinic. Eur J Neurol, 2001. 8: p. 601-611.
3. Patwardhan, N., Implanted ventricular shunts in the United States: the billion dollar a year cost of hydrocephalus treatment. Neurosurgery, 2005. 56: p. 139-145.
4. Zorc, J., et al., Radiographic evaluation for suspected cerebrospinal fluid shunt obstruction. Pediatr Emerg Care, 2002. 18: p. 337-340.
5. Laurence, K. and S. Coates, The natural history of hydrocephalus. Arch Dis Child, 1962. 37: p. 345-362.
6. Eckstein, H. and G. Macnab, Myelomeningocoele and hydrocephalus: the impact of modern treatment. Lancet, 1966. i: p. 842-845.
7. Shurtleff, D., R. Kronmal, and E. Foltz, Follow-up comparison of hydrocephalus with and without meningocoele. J Neurosurg, 1975. 42: p. 61-68.
8. McCullough, D. and L. Balzer-Martin, Current prognosis in overt neonatal hydrocephalus. J Neurosurg, 1982. 57: p. 378-383.
9. Iskandar, B., et al., Pitfalls in the diagnosis of ventricular shunt dysfunction: radiology reports and ventricular size. Pediatrics, 1998. 101: p. 1031-1036.
10. Forrest, D. and D. Cooper, Complications of ventriculoatrial shunts. J Neurosurg, 1968. 29: p. 506-512.
11. Amacher, A. and J. Wellington, Infantile hydrocephalus: Long-term results of surgical therapy. Child's Brain, 1984. 11: p. 217-229.
12. Staal, M., M. Meihuizen-de Regt, and J. Hess, Sudden death in hydrocephalic spina bifida aperta patients. Pediatr Neurosci, 1987. 13: p. 13-18.
13. O'Brien, M. and M. Harris, Long-term results in the treatment of hydrocephalus. Neurosurg Clin N Am, 1993. 4: p. 625-632.
14. Iskandar, B., et al., Death in shunted hydrocephalic children in the 1990s. Pediatr Neurosurg, 1998. 28: p. 173-176.
15. Drake, J., et al., Randomized trial of cerebrospinal fluid shunt valve design in pediatric hydrocephalus. Neurosurgery, 1998. 43: p. 294-305.

16. Kestle, J., et al., Lack of benefit of endoscopic ventriculoperitoneal shunt insertion: a multicenter randomized trial. J Neurosurg, 2003. 98: p. 284-290.
17. McGirt, M., et al., Shunt survival and etiology of failures. Pediatr Neurosurg, 2002. 36: p. 248-255.
18. Collins, P., A. Hockley, and D. Woollam, Surface ultrastructure of tissues occluding ventricular catheters. J Neurosurg, 1978. 48: p. 609-613.
19. Sainte-Rose, C., Shunt obstruction: A preventable complication? Pediatr Neurosurg, 1993. 19: p. 156-164.
20. Ventureyra, E. and M. Higgins, A new ventricular catheter for the prevention and treatment of proximal obstruction in cerebrospinal fluid shunts. Neurosurgery, 1994. 34: p. 924-926.
21. Piatt, J., Physical examination of patients with cerebrospinal fluid shunt: is there useful information in pumping the shunt? Pediatrics, 1992. 89: p. 470-473.
22. Noetzel, M. and R. Baker, Shunt fluid evaluation: risks and benefits in the evaluation of shunt malfunction and infection. J Neurosurg, 1984. 61: p. 328-332.
23. Sood, S., et al., Useful components of the shunt tap test for evaluation of shunt malfunction. Childs Nery Sys, 1993. 9: p. 157-161.
24. Watkins, L., et al., The diagnosis of blocked cerebrospinal fluid shunts: a prospective study of referral to a pediatric neurosurgical unit. Childs Nery Sys, 1994. 10: p. 87-90.
25. Gilday, D. and J. Kellam, 111DPTA evaluation of CSF diversionary shunts in children. J Nucl Med, 1973. 14: p. 683-686.
26. Howman-Giles, R., et al., A radionuclide method of evaluating shunt function and CSF circulation in hydrocephalus. J Neurosurg, 1984. 61: p. 604-605.
27. Vernet, 0., et al., Radionuclide shuntogram; adjunct to manage hydrocephalic patients. J Nucl Med, 1996. 37: p. 406-410.
28. Brendel, A., et al., Cerebrospinal shunt flow in adults: radionuclide quantitation with emphasis on patient position. Radiology, 1983. 149: p. 815-818.
29. Winter, G., Some factors affecting skin and wound healing. J Tissue Viability, 2006. 16: p. 20-23.
30. Avon, S. and R. Wood, Porcine skin as an in-vivo model for ageing of human bite marks. J Forensic Odontostomatol, 2005. 23: p. 30-39.
31. Ferry, L., G. Argentieri, and D. Lochner, The comparative histology of porcine and guinea pig skin with respect to iontophoretic drug delivery. Pharmaceut Acta Hely, 1995. 70: p. 43-56.
32. Riviere, J., Isolated perfused porcine skin flap systems., in Models for Assessing Drug Absorption and Metabolism, R.T.B.e. al., Editor. 1996, Plenum Press: New York.
33. Netzlaff, F., et al., Comparison of bovine udder skin with human and porcine skin in percutaneous permeation experiments. Altern Lab Anim, 2006. 34: p. 499-513.
34. Eggleston, T., et al., Comparison of two porcine (Sus scrofa domestica) skin models for in vivo near-infrared laser exposure. Comp Med, 2000. 50: p. 391-397.
35. Cohen, M., Measurement of the thermal properties of human skin. J Invest Dermatol, 1977. 69: p. 333-338.
36. Pitteti R. 2007. Emergency department evaluation of ventricular shunt malfunction: is the shunt series really necessary? Pediatr. Emerg. Care 23: 137-141.
37. Sood S, Canady A I, Harn, SD. 2000. Evaluation of shunt malfunction using shunt site reservoir. Pediatr. Neurosurg. 32: 180-186.
38. Hidaka M, Matsumae M, Kaoru I. Tsugane R. Saito I, 1995. Dynamic measurement of the flow rate in cerebrospinal fluid shunts in hydrocephalic patients. Eur. J. Nucl. Med. 28: 888-893.
39. Drake J, Sainte-Rose C, DaSilva M, Hirsh J-F, 1991. Cerebrospinal Fluid Flow Dynamics in Children with External Ventricular Drains. Neurosurgery. 28:242-250
40. Brenner D, Hall E, 2007, Computed Tomography—An Increasing Source of Radiation Exposure. N Engl J Med 2007; 357:2277-84
41. C. Nilsson, F Stahlberg, The nocturnal increase in human cerebrospinal fluid production is inhibited by a beta-1 receptor antagonist, Am J Physiol, December; 267:R1445-8, 1994
42. Mikael Edsbagge et al, Spinal CSF absorption in Healthy individuals, Am J Physiol, December; 287: R1450-1455, 2004
43. Lang E W, Chesnut R M. Intracranial pressure and cerebral perfusion pressure in severe head injury. New Horizons 3:400-409, 1995
44. Gopinath S P, Contant C F, Robertson C S et al. Critical thresholds for physiologic parameters in patients with severe head injury. Congressof Neurological Surgeons Annual Meeting. Vancouver, 1993
45. L. A. Steiner and P. J. D. Andrews Monitoring the injured brain: ICP and CBF British Journal of Anaesthesia 2006 97(1):26-38;
46. Jean-Luc Gennisson, Th̀erese Baldeweck, Mickael Tanter, Stefan Catheline, Mathias Fink, Laurent Sandrin, C̀eline Cornillon, and Bernard Querleux, Assessment of Elastic Parameters of Human Skin Using Dynamic Elastography IEEE transactions on ultrasonics, ferroelectrics, and frequency control, vol. 51, no. 8, August 2004
47. Alan J Lupin, Rachel J. Gardiner. Scalp thickness in the temporal region: its relevance to the development of cochlear implants Cochlear Implants 2. International Vol. 2, no. 1, 2001.
48. Adam Bromby, Zofia Czosnyka, David Allin, Hugh K Richards, John D Pickard and Marek Czosnyka. Laboratory study on "intracranial hypotension" created by pumping the chamber of a hydrocephalus shunt. Cerebrospinal Fluid Research March 2007, 4:2

What is claimed is:

1. An apparatus for detecting the degree of occlusion in an implanted cerebrospinal fluid (CSF) shunt having a shunt valve in symptomatic or asymptomatic, said apparatus comprising:
a pad that is adapted to be placed against the skin of a patient over the location of the CSF shunt, said pad comprising a plurality of temperature sensors that are aligned in a first direction and wherein one of said plurality of temperature sensors is aligned with the CSF shunt, each of said temperature sensors generating respective temperature data;
a vibrating device that applies pulsation energy against the shunt valve for a predetermined period when said vibrating device is positioned against the skin over said shunt valve; and
a sensor processing device that is electrically coupled to said pad for receiving temperature data from each of said temperature sensors, said sensor processing device using said temperature data to determine the degree of occlusion of said CSF shunt when a temperature source is applied to said pad for said predetermined period of time.

2. A method for detecting the degree of occlusion in an implanted cerebrospinal fluid (CSF) shunt having a shunt valve in symptomatic or asymptomatic patients, said method comprising:

applying a plurality of temperature sensors against the skin over the location of the CSF shunt and aligned in a first direction, and wherein only one of said plurality of temperature sensors is aligned with the CSF shunt;

applying a temperature source over the CSF shunt and upstream of said plurality of temperature sensors for a predetermined period;

applying a vibrating device against the skin positioned over the shunt valve for applying a pulsation procedure for said predetermined period of time;

collecting temperature data from said plurality of temperature sensors during said predetermined period of time;

determining the degree of occlusion in said CSF shunt based on said collected data.

3. The method of claim 2 wherein said step of determining the degree of occlusion in said CSF shunt comprises:
 (a) detecting no change of temperature in said collected data over said predetermined period; and
 (b) establishing said degree of occlusion to be obstructed.

4. The method of claim 2 wherein said step of determining the degree of occlusion comprises:
 (a) detecting a change of temperature in said collected data over said predetermined period; and
 (b) establishing said degree of occlusion to be unobstructed.

5. The method of claim 4 wherein said temperature source is a cold source and wherein said step of detecting a change in temperature comprises detecting a transcutaneous change in temperature as cooled CSF flows through said CSF shunt.

6. The method of claim 2 wherein said step of determining said degree of occlusion comprises:
 (a) detecting changes of temperature in said collected data;
 (b) correlating said changes of temperature with CSF shunt resistance; and
 (c) defining a plurality of CSF shunt resistance levels comprising full patency, partial occlusion and complete occlusion based upon said correlation.

7. The method of claim 6 wherein said degree of occlusion is determined for symptomatic patients.

8. The method of claim 6 wherein said degree of occlusion is determined for asymptomatic patients.

9. The method of claim 6 wherein said step of correlating said changes of temperature with CSF shunt resistance comprises activating said vibrating device at two distinct times using respective frequencies.

10. The method of claim 6 wherein said step of correlating said changes of temperature with CSF shunt resistance comprises:
 (a) activating said vibrating device;
 (b) monitoring CSF flow rates generated by said vibrating device activation using said temperature data; and
 (c) assessing changes in said CSF flow rates with said CSF shunt resistance.

11. The method of claim 6 further comprising the step of tracking CSF shunt resistance to detect possible shunt obstruction early.

12. A method for tracking shunt resistance in order to detect possible cerebrospinal fluid (CSF) shunt obstruction in a CSF shunt, having a shunt valve, implanted within a patient, said method comprising:

applying a plurality of temperature sensors against the skin over the location of the CSF shunt and aligned in a first direction, and wherein only one of said plurality of temperature sensors is aligned with the CSF shunt;

applying a temperature source over the CSF shunt and upstream of said plurality of temperature sensors for a predetermined period;

applying a vibrating device against the skin positioned over the shunt valve for applying a pulsation procedure for said predetermined period of time;

collecting temperature data from said plurality of temperature sensors during said predetermined period of time;

identifying a maximum temperature drop; and comparing said maximum temperature drop to a look up table that correlates shunt resistance therewith.

\* \* \* \* \*